United States Patent [19]
Kerr

[11] Patent Number: 6,015,422
[45] Date of Patent: Jan. 18, 2000

[54] COLLAPSIBLE LOW-PROFILE VASCULAR GRAFT IMPLANTATION INSTRUMENT AND METHOD FOR USE THEREOF

[75] Inventor: Andrew Kerr, New York, N.Y.

[73] Assignee: Montefiore Hospital and Medical Center, Bronx, N.Y.

[21] Appl. No.: 09/025,713

[22] Filed: Feb. 18, 1998

[51] Int. Cl.[7] .................................................. A61M 29/00
[52] U.S. Cl. ............................................................. 606/191
[58] Field of Search .................................. 606/191, 198, 606/194; 623/1; 604/104

[56] References Cited

U.S. PATENT DOCUMENTS

| | | |
|---|---|---|
| 4,140,126 | 2/1979 | Choudhury . |
| 4,562,596 | 1/1986 | Kornberg . |
| 4,938,740 | 7/1990 | Melbin . |
| 5,104,399 | 4/1992 | Lazarus . |
| 5,116,318 | 5/1992 | Hillstead ............................ 606/191 |
| 5,151,105 | 9/1992 | Kwan-Gett ........................ 606/191 |
| 5,207,695 | 5/1993 | Trout, III . |
| 5,219,355 | 6/1993 | Parodi et al. . |
| 5,258,020 | 11/1993 | Froix . |
| 5,290,305 | 3/1994 | Inoue . |
| 5,464,449 | 11/1995 | Ryan et al. . |
| 5,507,770 | 4/1996 | Turk . |
| 5,554,182 | 9/1996 | Dinh et al. . |
| 5,562,725 | 10/1996 | Schmitt et al. . |
| 5,591,195 | 1/1997 | Taheri et al. . |
| 5,617,878 | 4/1997 | Taheri .................................... 623/1 |
| 5,628,782 | 5/1997 | Myers et al. . |
| 5,643,309 | 7/1997 | Myler et al. . |
| 5,667,522 | 9/1997 | Flomenblit et al. . |
| 5,676,696 | 10/1997 | Marcade . |
| 5,713,948 | 2/1998 | Uflacker ................................ 606/194 |
| 5,776,186 | 7/1998 | Uflacker . |
| 5,824,055 | 10/1998 | Spiridigliozze et al. . |

*Primary Examiner*—Jeffrey A. Smith
*Assistant Examiner*—Eduardo C. Robert
*Attorney, Agent, or Firm*—Anthony J. Casella; Gerald E. Hespos

[57] ABSTRACT

An instrument is provided for supporting a tubular vascular graft during endovascular implantation and methods for use thereof. In one embodiment, the instrument is formed from two flexible guidewires bent to each define a loop and two straight portions. In a second embodiment, the instrument is formed from two flexible guidewires bent to define outwardly-biased tines, wherein, threads are sewn to portions of the vascular graft and connected to the tines. The instrument is collapsible due to the flexibility of the guidewires used to form the instrument. In an uncollapsed state, with a length of graft material being mounted to the instrument, the loops or tines may bias the graft into a semi-expanded state with a passage being defined through the graft. An unexpanded stent is introduced into the passage of the semi-expanded graft to both further expand the graft and provide reinforcement. A distensible device is also used with the preferred method of using the invention to accomplish full circumferential expansion of the graft and stent assembly and to facilitate removal of the instrument.

16 Claims, 3 Drawing Sheets

COLLAPSIBLE LOW-PROFILE VASCULAR GRAFT IMPLANTATION INSTRUMENT AND METHOD FOR USE THEREOF

BACKGROUND OF THE INVENTION

1. Field of the Invention

This invention relates to devices and methods for endovascular treatment of blood vessel anomalies and, more particularly, for the implantation of vascular grafts.

2. Description of the Prior Art

Blood vessel anomalies, such as aneurysms, stenoses, etc., have been treated in the prior art through surgical procedures, wherein the diseased portion of the blood vessel may be ablated and replaced with a prosthetic member, such as shown in U.S. Pat. No. 4,938,740 to Melbin. An improvement over this technique which obviates the need for open surgery is directed to the endovascular placement of a stent-reinforced graft. The stent and graft is entered into the bloodstream from a remote puncture site, typically through the neck or femoral region, via a catheter in an unexpanded state to facilitate movement thereof through the blood vessel. The stent/graft assembly is aligned in the blood vessel using techniques known by those skilled in the art such that the assembly extends between healthy portions of the blood vessel and by-passes the blood vessel anomaly. Once properly aligned, the stent and graft are caused to expand thereby engaging axially-spaced sections of healthy blood vessel wall and defining an enclosed pathway for blood flow through the anomaly. If, for example, a graft was disposed in such a manner to by-pass an aneurysm and such aneurysm ruptured, the emplaced graft would act as a conduit to maintain a continuous flow of blood through the ruptured portion of blood vessel.

Different devices are in the prior art which allow for endovascular movement of a stent and/or graft and expansion thereof. First, devices exist adapted to selectively elongate and foreshorten a length of tubular graft material, resulting in a corresponding change in diameter of the graft, such as in U.S. Pat. No. 5,464,449 to Ryan et al. Alternatively, a stent and/or graft may be directly disposed on an expandable angioplasty balloon, as shown in U.S. Pat. No. 5,554,182 to Dinh et al. Finally, self-expanding stents and/or grafts are known in the prior art which are spring-biased or formed of temperature sensitive material. An example of this third type of prior art is found in U.S. Pat. No. 5,562,725 to Schmitt et al.

The prior art, however, has some deficiency in providing for implantation of a stent-reinforced graft. The mounting of the graft onto a stent, in addition to a control mechanism or an angioplasty balloon, results in the graft defining a relatively significant outer dimension. As is readily appreciated, due to the small dimensions of blood vessel lumens, it is desirable to keep the profile of all endovascular devices to a minimum. Also, lower profile instruments are more easily manipulated through blood vessels, than larger profile instruments especially through blood vessels which may contain accumulated plaque.

It is an object of the subject invention to provide a collapsible support for a vascular graft which allows for low-profile insertion thereof.

It is also an object of the subject application to provide a support for maintaining a graft in a semi-expanded state with sufficient space within the graft to preferably accommodate an unexpanded stent.

SUMMARY OF THE INVENTION

The aforementioned objects are met by a frame for supporting a vascular graft. In a first embodiment, the frame is formed from two flexible angiographic guidewires bent to define two spaced-apart loops, the loops being dimensioned to support the graft in a semi-expanded state.

The angiographic guidewires may be of any resilient type known to those skilled in the art which is formed to have memory, i.e., being capable of, upon deformation, generally returning to a pre-deformation shape. Each guidewire is bent to define, in a natural state, a loop and a segment with the segment including a generally straight first portion extending from the loop, and a generally straight second portion extending from the first portion and through the supported vascular graft. The loops are formed with frangible connections, such as through welding, which allow for the loops to be respectively torn open upon sufficient application of force. Further, the second portions of both guidewires are joined together along the respective lengths thereof, with the joined second portions extending through the loops of both guidewires to define a common shaft of the instrument.

With the loops supporting the vascular graft, the loops are dimensioned to partially expand the graft circumferentialy and allow for passage of an unexpanded stent thereinto with the stent being threaded over the common shaft. In this manner, the stent may be introduced inside the graft supported by the subject invention with circumferential expansion of the introduced stent further circumferentially expanding the partially-expanded graft.

The first embodiment is preferably used in conjunction with self-expanding stents. As described below, if a self-expanding stent is utilized, a distensible device, such as a angioplasty balloon, will be introduced separately from the stent to allow for proper removal of the invention and implantation of the graft. Alternatively, a stent may be utilized which is not self-expanding and requires mechanical force for expansion. In the alternative variation, the stent may be directly mounted to a distensible device, such as a angioplasty balloon.

In use of the first embodiment, a length of tubular graft material, any resilient graft material known to those skilled in the art which is expandable (e.g. PTFE), is mounted onto the invention with the loops being in engagement with the inner surface of the graft. The graft and the loops are then caused to be collectively collapsed with the graft being circumferentially compressed substantially about the common shaft and the loops being interposed between the graft and the common shaft in distorted states. Preferably, the graft and the loops are maintained in the collapsed position by a lubricious plastic being tightly disposed about the graft. Once collapsed, the assembly is introduced into the bloodstream and guided therethrough using techniques known to those skilled in the art. The graft is properly positioned in the desired location with the ends of the graft being aligned with healthy portions of blood vessel found at axially-spaced locations about the anomaly which is being treated. Thereafter, the lubricious plastic is removed from the graft, thus, allowing the loops to regain memory and bias the graft into a semi-expanded state, with a passage being defined through the graft.

With the graft being partially expanded, an unexpanded stent is introduced inside of the graft to provide reinforcement for supporting the graft. In the preferred variation of the first embodiment, a self-expanding stent is introduced inside of the semi-expanded graft by threading and advancing the stent over the common shaft of the invention. With the stent being aligned with the graft, the stent is allowed to expand, which causes the graft to be further expanded. Afterwards, a distensible device, such as an angioplasty balloon, is introduced inside of the semi-expanded stent and graft assembly. The distensible device is caused to be expanded which, in turn, causes the stent and graft assembly to become fully expanded with the graft coming into pressing engagement with healthy portions of the blood vessel wall. Simultaneously, the expansion of the distensible device will cause the frangible connections used to form the loops of the invention to break, thus breaking the loops. The distensible device is then deflated and withdrawn, and, finally, the invention is withdrawn from the blood vessel with the portions of the guidewires which define the loops being pulled out from between the expanded stent and expanded graft upon withdrawal of the invention. As a result of this procedure, a fully expanded stent-reinforced graft is implanted at a desired location in a blood vessel.

In alternate variations of the first embodiment of the invention, thread can be wrapped about the collapsed graft to maintain it in a closed position. Also, a non-self-expanding stent may be utilized which is directly mounted onto the distensible device.

In a second embodiment of the invention, the frame is formed from two flexible angiographic guidewires bent to define two outwardly biased tines. A loop of thread is knotted to the end of each tine which is sewn into portions of the graft material which is to be implanted. The threads prevent movement of the graft relative to the frame. As with the first embodiment, the angiographic guidewires, may be of any resilient type known to those skilled in the art which is formed to have memory. Each guidewire is bent to define, in a natural state, the tine extending from a segment. The segments are joined to define a common shaft for the instrument. The tines are biased so that the free ends of the tines are spaced from the common shaft of the instrument in a natural state. Also, the tines are formed with varying lengths to enable engagement of the graft at axially-spaced locations by the instrument. The thread is caused to engage the graft such that the movement of the graft relative to the instrument is minimized—e.g. the thread may be sewn into portions of the graft. The length of each thread must be less than the circumference defined by the inner surface of the graft in an expanded state. As such, upon expansion of the threads and the graft, the loops defined by the threads would rupture prior to the full circumferential expansion of the graft.

In use of the second embodiment, the graft is mounted to the instrument with the tines and threads engaging axially-spaced locations of the graft. The tines and the graft are both caused to be collapsed, with the graft being circumferentially compressed substantially about the common shaft and the tines being interposed between the graft and the common shaft in pressing engagement with the common shaft. As with the first embodiment, lubricious plastic is preferably wrapped about the collapsed graft to maintain it in the collapsed position. Alternatively, thread may be wound about the graft. Once the collapsed assembly is introduced into the bloodstream and, proprerly located the plastic is retracted thus exposing the graft. The bias of the tines will cause some circumferential expansion of the graft such that the graft comes into a semi-expanded state.

The second embodiment is used in the same manner as the first embodiment. An unexpanded self-expanding stent is preferably introduced into the semi-expanded graft and caused to expand. Likewise, a distensible device is also introduced. Upon expansion of the distensible device, the stent and graft become fully expanded and the loops formed by the threads become ruptured. Thereafter, the instrument is removed.

With respect to a third embodiment of the invention, the third embodiment actually encompasses variations of the first two embodiments. In one variation of the third embodiment, the structure of the first embodiment is provided, but the loops need not be formed with memory. Similarly, a second variation of the third embodiment is directed to the same structure of the second embodiment of the invention, but the tines need not be biased. In either variation of the third embodiment, the loops and tines are used to simply maintain the graft in a relatively fixed position along the common shaft of the instrument, but not formed to partially expand the graft. The loops of the structure of the first embodiment may, through frictional engagement, maintain the position of the graft. Likewise, the engagement of the thread-formed loops of the second embodiment may also prevent movement of the graft. With respect to the third embodiment, since the graft will not be forced into a semi-expanded state, the catheter which bears the first instrument inserted into the graft during the procedure of endovascular implantation (either a self-expanding stent or a combination of a stent and a distensible device) will be formed with a sharpened or ramped tip which will allow the catheter to slip into the unexpanded graft along with the device mounted to the catheter. Simultaneously, the catheter will slip through the loops of either embodiment also. The use of the third embodiment is the same as the first two embodiments in all other respects.

These and other features of the invention will be better understood through a study of the following detailed description and accompanying drawings.

DETAILED DESCRIPTION OF THE PREFERRED EMBODIMENTS

Figure 1:
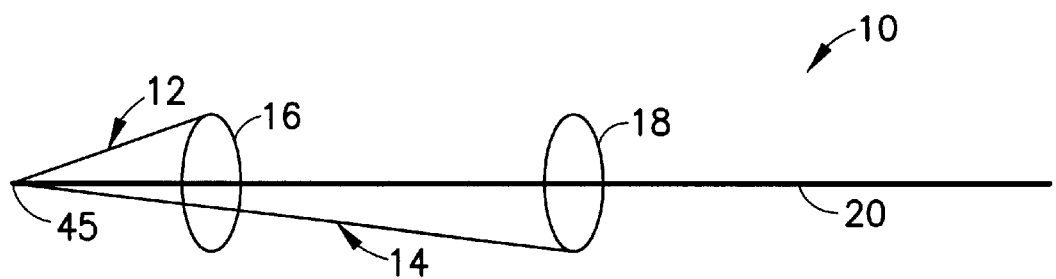
FIG. 1 is a plan view of the first embodiment of the invention.

Referring generally to FIGS. 1–11, the first embodiment of the invention is shown. In FIG. 1, an instrument 10 is depicted for supporting a vascular graft during endovascular implantation thereof. The instrument 10 is generally comprised of a first and a second flexible guidewire 12 and 14, respectively, with each guidewire being formed to generally define respectively loops 16 and 18 and a common shaft 20.

Figure 2:
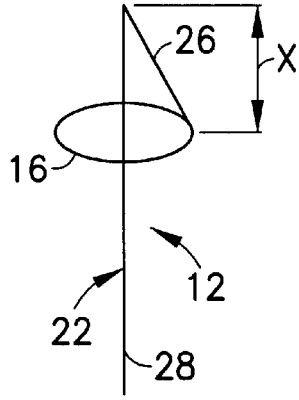
FIG. 2 is a plan view of the first guidewire used to form the first embodiment of the invention.
Figure 2A:
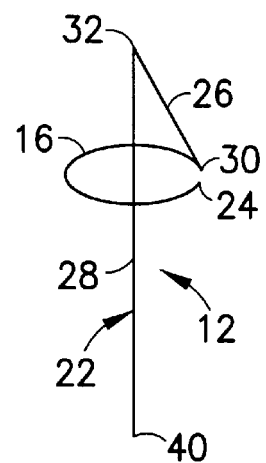
FIG. 2a is a plan view of the first guidewire with the loop being discontinuous to show the construction thereof.

The guidewires 12, 14 are to be formed of any resilient type of material known to those skilled in the art which is formed to have memory, i.e., being capable of, upon deformation, generally returning to a pre-deformation shape. Referring to FIG. 2, the first guidewire 12 is bent to define the loop 16 and a segment 22 extending from the loop 16. The first guidewire 12 is formed from one continuous length of guidewire with a predetermined length of guidewire extending from one end 24 defining the loop 16. The segment 22 includes a first portion 26 and a second portion 28. FIG. 2a depicts the first guidewire 12 with the loop 16 not being closed to illustrate the formation of the first guidewire 12. As shown in FIG. 2a, the first guidewire 12 is bent from the first end 24 to generally define the arcuate shape of the loop 16, further bent about the corner 30 to define the first portion 26, and further bent about corner 32 to define the second portion 28. The corner 32 is preferably rounded, not sharp. The loop 16 is closed with the first end 24 being frangibly connected to the corner 30. The strength of the frangible connection is as described below.

Figure 3:
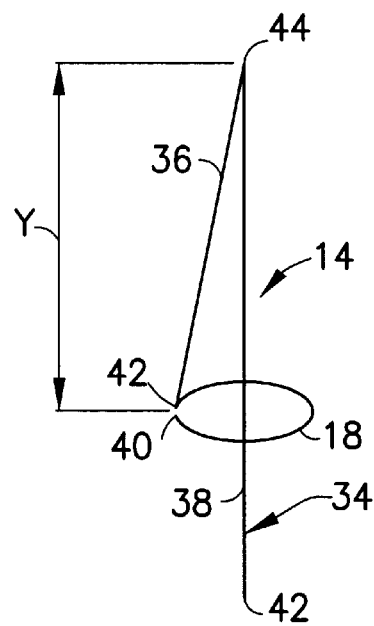
FIG. 3 is a plan view of the second guidewire used to form the first embodiment of the invention.

The second guidewire 14 is generally formed in the same manner as the first guidewire 12. Specifically, as shown in FIG. 3, the second guidewire 14 is formed from a continuous length of guidewire bent to define the loop 18, and a segment 34, which includes a first portion 36 and a second portion 38. Similar to the first guidewire 12, the second guidewire 14 is bent to define the loop 18 from one end 40, about a corner 42 to define the first portion 36, and about a corner 44 to define the second portion 38. The corner 44 is preferably rounded. Again, similar to the loop 16 of the first guidewire 12, the loop 18 is closed due to a frangible connection between the end 40 and the corner 42, wherein the strength of the frangible connection is also discussed below.

The instrument 10 is formed by joining the second portion 28 of the first guidewire 12 and the second portion 38 of the second guidewire 14, with the corners 32 and 44, respectively, of the guidewires being aligned. The joined first portions 28 and 38 collectively define the common shaft 20 of the instrument 10, and, the corners 32 and 44 collectively define a tip 45 of the instrument 10. As shown in FIG. 1, the common shaft 20 is disposed to extend through both of the loops 16 and 18. The length of the common shaft 20, as measured extending from the tip 45, is determined by the length necessary to properly position and manipulate the instrument 10 from a location external of the puncture site, as described below. As is readily apparent, the length of the common shaft 20 is determined by the respective lengths of the second portions 28 and 38.

The loops 16 and 18 are preferably elliptically formed, but may also be formed to define other shapes. Also, the loops 16 and 18 are preferably formed to generally define the same dimensions. In forming the instrument 10, however, it is desired that the loops 16 and 18 be located at axially-spaced locations relative to the common shaft 20. To this end, in forming the first guidewire 12, the length of the first portion 26 is defined such that the loop 16 is located a distance "x" from the corner 32, and the loop 18 of the second guidewire 14 is formed a distance "y" from the corner 44, with the distance "y" being greater than the distance "x". The actually spacing between the loops 16 and 18 is dependent upon the length of the vascular graft which is to be supported by the instrument 10. Preferably, the loops 16 and 18 are located in proximity to the ends of the vascular graft.

It should be noted that although the first embodiment is disclosed as being formed with two loops 16, 18, any number of loops could be used. It is preferred, however, that the loops be located to ensure that at least the end of the vascular graft into which the stent is to be inserted, as described below, will be biased open.

It should also be noted that although the respective first portions 26 and 36 of the guidewires 12 and 14 are shown to be generally straight, the second portions 26 and 36 need only extend between the respective corners 32 and 44 to the respective corners 30 and 40 and need not be formed to be generally straight. As such, the first portions 26 and 36 extend continuously angularly relative to the common shaft 20 between the respective corners 32 and 44 to the respective corners 30 and 40.

Figure 4:
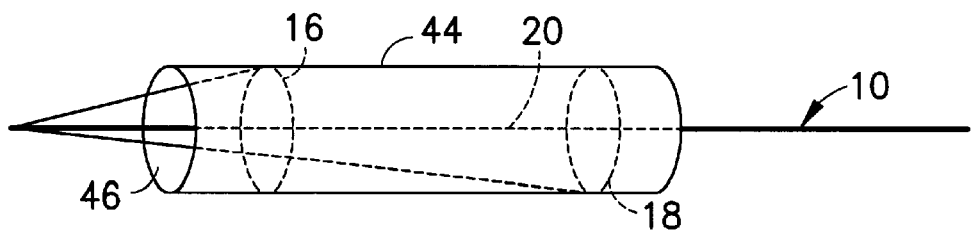
FIG. 4 is a plan view of the first embodiment of the invention with a vascular graft being mounted thereto.

FIG. 4 shows a length of tubular vascular graft 44 mounted onto the instrument 10, with the loops 16, 18 being in pressing engagement with the inner surface 46 of the graft 44. The vascular graft 44 may be of any resilient type known to those skilled in the art. The memory of the loops 16 and 18 cause the graft 44 to be at least partially expanded such that, as shown in FIG. 4, a passage is formed through the graft 44 about the common shaft 20 which is large enough to accommodate the unexpanded stent (discussed below) intended to be used with the instrument 10. In natural states, as shown in FIGS. 2 and 3, the loops 16 and 18 must be formed with dimensions which are at least as great as the dimensions required to allow passage of the unexpanded stent into the graft 44—i.e. the loops 16, 18 must be dimensioned such that the memory of the loops 16, 18 will at least provide for sufficient expansion of the graft 44 to allow for passage of the unexpanded stent into the graft 44.

Figure 5:
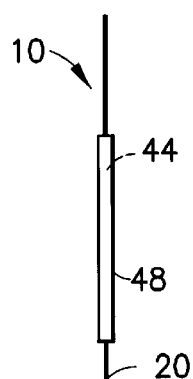
FIG. 5 is a plan view of the invention in collapsed state with plastic being wrapped thereabout.
Figure 6:
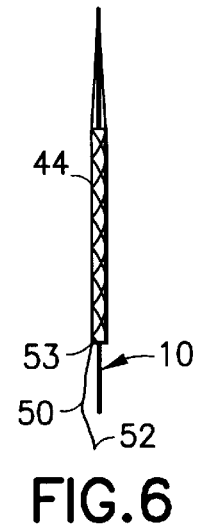
FIG. 6 is a plan view of the invention in a collapsed state with thread being wrapped thereabout.

To facilitate implantation of the graft 44 in a desired location in a blood vessel, the instrument 10 and graft 44 are collectively caused to be circumferentially collapsed, about the common shaft 20 as shown in FIGS. 5–6. Referring specifically to FIG. 5, the collective assembly of the instrument 10 and the graft 44 can be maintained in a collapsed position by disposing a lubricious plastic overwrap 48 tightly about the outer surface of the graft 44. Any lubricious plastic known to those skilled in the art, such as hydrophilic plastics, which is sufficiently strong to resist outward circumferentially-generated pressure due to the tendency of the loops 16 and 18 to regain memory may be utilized. The lubricity of the plastic 48 allows for easy removal thereof from the graft 44 by simply urging the plastic 48 rearwardly, using techniques known in the prior art, in a direction along the axis of the common shaft 20, thus causing it to slip off the graft 44. Alternatively, referring to FIG. 6, a thread 50 may be wound about the collapsed instrument 10 and the graft 44 with the thread 50 having sufficient length to have one end 52 extend externally from the puncture site. The other end 53 of the thread 50 is knotted to a point along the intermediate length of the thread 50 such that a jerk of the thread 50 at the end 52 will cause the knot formed by the end 53 to break and the entire thread 50 can be withdrawn. In FIG. 6, the thread 50 is shown as being passed over the tip 45 of the instrument 10, however, the thread 50 may be wound about the graft 44 in other configurations.

Figure 7:
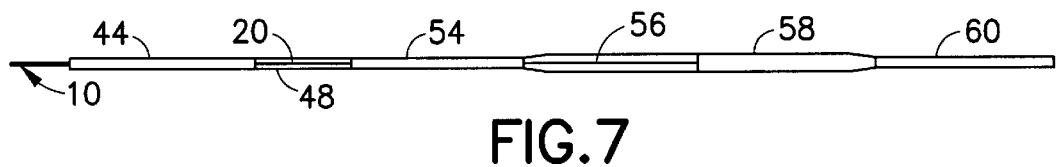
FIG. 7 is a plan view of the invention arranged with an unexpanded stent and unexpanded distensible device.

FIG. 7 shows a preferred arrangement for using the instrument 10 in implanting the graft 44. Referring to FIG. 7 and going from the left to the right of the figure, the device 10 is shown having the graft 44 mounted thereto, the graft 44 and the instrument 10 being both collapsed. Although not shown, a tubular stiffener, known in the prior art, is preferably disposed over the common shaft 20, extending from the tip 45 to the free end of the common shaft 20. The stiffener is disposed adjacent the common shaft 20 to provide rigidity thereto. The lubricious plastic 48 (shown to be transparent) is wrapped about the collapsed graft 44, in a similar manner as that shown in FIG. 5. In contrast to FIG. 5, the plastic 48 extends beyond the graft 44 in a rightward direction to encapsulate further elements. An unexpanded self-expanding stent 54 is located to the right of the graft 44 which is mounted to a catheter 56. Any type of self-expanding stent, such as temperature-sensitive stents, may be used with the invention. The catheter 56 is thread onto the common shaft 20 so that the stent 54 is slidable along the length thereof. To the right of the stent 54 is located an unexpanded distensible device 58, preferably, an angioplasty balloon. The distensible device 58 is mounted onto a catheter 60, which in turn, is threaded onto the catheter 56. The lubricious plastic 48 is extended over the stent 54 and the distensible device 58, in addition to the graft 44, to not only maintain the graft 44 in a collapsed position, but also prevent expansion of the stent 54 and the distensible device 58. It can be readily appreciated that the low-profile arrangement shown in FIG. 7 allows for relative movement of the graft 44, the stent 54 and the distensible device 58 relative to one another. To allow for such independent movement during use, the common shaft 20, the catheter 56 and the catheter 60 must be formed with lengths extending in a rightward direction sufficiently to allow for a physician to manipulate the various devices externally of the puncture site.

Figure 8:
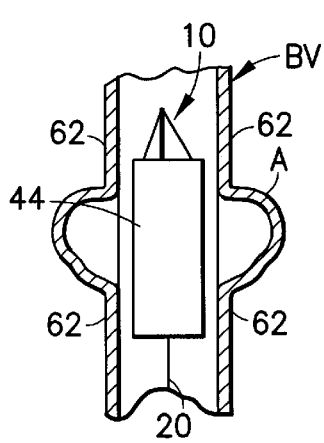
FIGS. 8–10 show schematically the use of the first embodiment to endovascularly implant a graft to by-pass an aneurysm.
Figure 9:
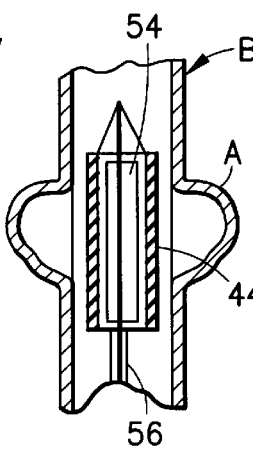
Figure 10:
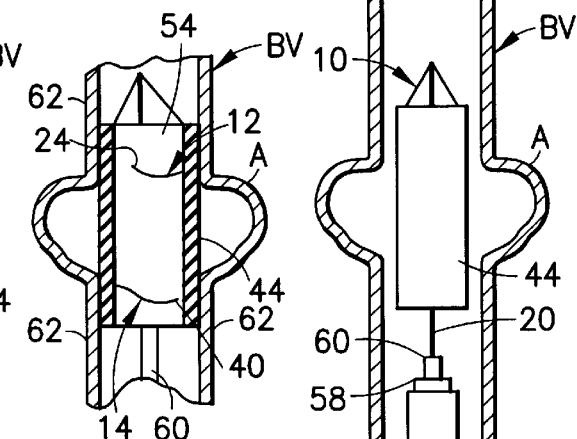
Figure 11:
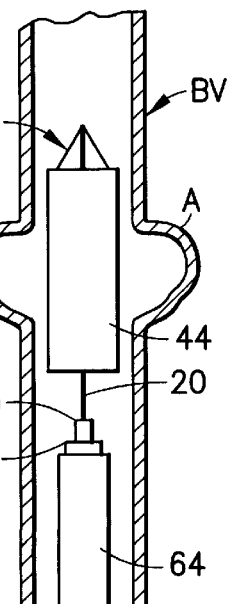
FIG. 11 is a schematic of an arrangement of a variation of the first embodiment wherein a stent is directly mounted onto a distensible device.
Figure 12:
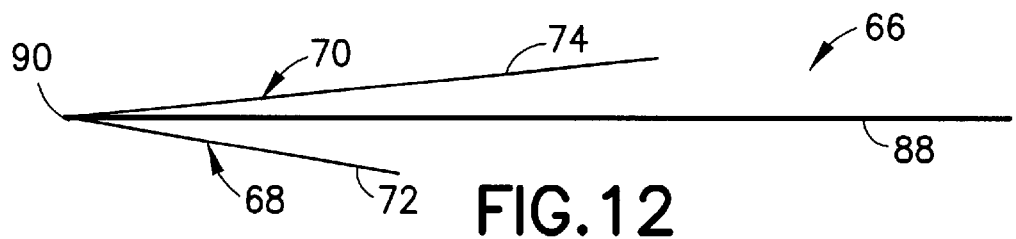
FIG. 12 is a plan view of the second embodiment of the invention.

FIGS. 8–10 schematically depict an exemplary use of the invention. A portion of a blood vessel BV is shown in which an aneurysm A is formed which is to be by-passed by a stent-reinforced vascular graft. Although FIGS. 8–10 show an application of the invention with respect to the aneurysm A, the invention can be used to treat other blood vessel anomalies which can be treated through the endovascular implantation of a stent-reinforced vascular graft. In the first stage of use, the low-profile assembly shown in FIG. 7 is introduced into the blood vessel BV from a remote puncture site. Using techniques known by those skilled in the art, such as fluoroscopy, the instrument 10 is aligned to by-pass the aneurysm A such that the graft 44 extends between axially-spaced healthy portions of the blood vessel BV, generally designated by the numeral 62. Once aligned, the lubricious plastic 48 is caused to be retracted relative to the vascular graft 44, thus exposing the vascular graft 44. Consequently, the loops 16 and 18 (not shown) regain some memory and bias the graft 44 into a semi-expanded state, which is similar to the state shown in FIG. 4.

Referring to FIG. 9, the stent 54 is then advanced over the common shaft 20 into the semi-expanded graft 44 with the lubricious plastic 48 being thereabout. Afterwards, the plastic 48 is retracted to expose the stent 54, thus allowing the stent 54 to circumferentially self-expand within the loops 16 and 18 and the graft 44. The strength of the frangible connections used to form the loops 16 and 18 is determined by the degree of force which may be generated by the expansion of the stent 54. Preferably, the loops 16 and 18 are provided with frangible connections which can withstand the circumferential expansion of the stent 54, but which can be broken by expansion of the distensible device 58. Alternatively, although not desired, the loops 16 and 18 may be formed with frangible connections which can be ruptured by the expansion of the stent 54, thus obviating the need for the distensible device 58. It should be noted, however, that with such an alternative construction, the frangible connections would be weaker than in the preferred embodiment and may be susceptible to failure. Further, if no distensible device is to be utilized, the stent 54 must be capable of fully expanding the graft 44. If the stent 54 is capable of generating a substantial degree of force due to expansion and fully expanding the graft 44, thus allowing for stronger frangible connections, the alternative embodiment could become a desirable alternative.

In the first embodiment, the stent 54 must sufficiently expand within the loops 16, 18 so that a passage is defined therethrough which is sufficient to accommodate the unexpanded distensible device 58. Thereafter, the distensible device 58 is exposed by the plastic 48 and advanced into the passage defined by the stent 54. Using techniques known by those skilled in the art, the distensible device 58 is cause to expand, simultaneously causing the full expansion of the graft 44 and the stent 54. Consequently, the outer surface of the graft 44 comes into pressing engagement with the healthy portions 62 of the blood vessel BV. The expansion of the distensible device 58 also causes rupture of the frangible connections used to respectively form the loops 16 and 18. Upon rupture of the frangible connections, as shown in FIG. 10, the portions of the first and second guidewires 12 and 14 which extend from the respective ends 24 and 40 to form the loops 16 and 18, respectively, are interposed between the expanded stent 54 and the expanded graft 44. The common shaft 20 is then retracted thus causing the first and second guidewires 12 and 14 to be drawn from between the stent 54 and the graft 44 and through the catheter 60 which supports the expanded distensible device 58. Finally, the distensible device 58 is deflated and withdrawn, leaving the expanded stent-reinforced graft 44 in the blood vessel BV.

In a variation of the first embodiment, a non-self-expanding stent 64 may be utilized with the instrument 10. The stent 64 may be directly mounted onto the distensible device 58 which relies upon the distensible device 58 for force to facilitate expansion thereof. In use, the instrument 10 and the graft 44 may be maintained in a collapsed state through either the use of the lubricious plastic 48 or the thread 50. Similar to the above-described procedure, the graft 44 is aligned relative to the aneurysm A which is to be treated and caused to be semi-expanded. The graft 44 must be sufficiently expanded to facilitate entry of the combined stent 64 and distensible device 58 assembly. The stent 64 is advanced into the graft 44, along with the distensible device 58, through the manipulation of the catheter 60. Thereafter, the distensible device 58 is caused to expand, with simultaneous expansion of the stent 64, the graft 44 and the rupturing of the frangible connections used to form the loops 16 and 18. As described above, the instrument 10 and the distensible device 58 are then withdrawn.

Referring generally to FIGS. 12–16, the second embodiment of the invention is shown therein. An instrument 66 is provided for supporting the graft 44 during an endovascular implantation thereof. The instrument 66 is formed from first and second flexible guidewires 68, 70, each being bent to define outwardly-biased tines 72, 74.

Figure 13:
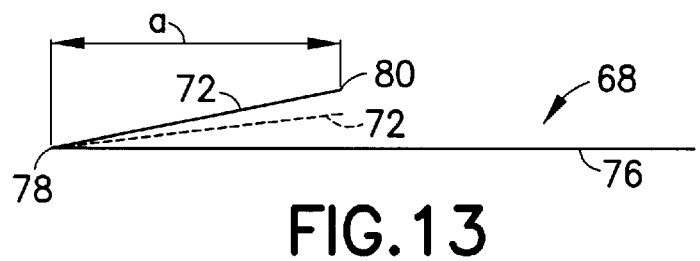
FIG. 13 is a plan view of the first guidewire used to form the second embodiment of the invention.

As more clearly shown in FIG. 13, the first guidewire 68 is formed from one continuous length of guidewire which is bent to define the tine 72 and a segment 76. The tine 72 and the segment 76 are joined at corner 78. The corner 78 is preferably rounded. The first guidewire 68 is formed from a naturally resilient material which generates a bias about the corner 78 to cause a free end 80 of the tine 72 to be spaced from the segment 76 in a natural state. As shown in dashed lines in FIG. 13, the corner 78 provides a hinged connection about which the tine 72 may pivot relative to the segment 76.

Figure 14:
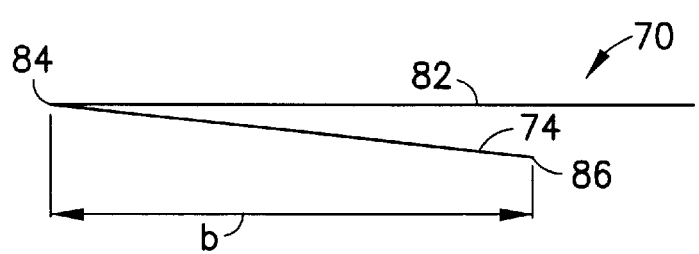
FIG. 14 is a plan view of the second guidewire used to form the second embodiment of the invention.

Referring to FIG. 14, the second guidewire 70 is shown, which is basically shaped and constructed in the same fashion as the first guidewire 68. Specifically, the second guidewire 70 is formed with the tine 74 being connected to a segment 82 about a corner 84. The corner 84 is preferably rounded. As with the construction of the first guidewire 68, the tine 74 is formed with a free end 86 which is biased to be spaced from the segment 82.

The instrument 66 is formed by joining the segments 76 and 82 to define a common shaft 88. In forming the common shaft 88, the corners 78 and 84, respectively, are aligned to form a tip 90 of the instrument. As described above, and with respect to the first embodiment, and referring to FIG. 12, the common shaft 88 must be provided with a sufficient length in the rightward direction which would allow a physician to operate the instrument 66 from a location external the puncture site. The length of the common shaft 88 is a direction function of the lengths of the segments 76 and 82.

Figure 16:
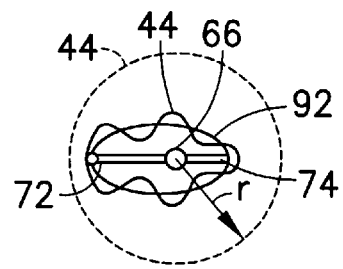
FIG. 16 is a side view of the second embodiment of the invention with a vascular graft being mounted thereto.

As with the first embodiment of the invention, it is desired that the instrument 66 engage axially-spaced apart locations of the graft 44. To achieve this end, the tines 72 and 74 must be formed of different lengths. As shown in FIG. 13, the tine 72 is formed to define a distance "a" from the corner 78 to the free end 80. In a similar manner, as shown in FIG. 14, the tine 74 is formed to define a distance "b" from the corner 84 to the free end 86. It is preferred that the distance "b" be greater than the distance "a" to ensure engagement at axially-spaced locations of the graft 44. The distance "b", however, could equal the distance "a". Also, in forming the instrument 66, the tines 72, 74 are preferably oriented relative to the common shaft 88 to extend in opposing directions therefrom. Referring to FIG. 16, a side view of the instrument 66 is shown with the graft 44 being mounted thereon. As can be seen, the tines 72 and 74 are disposed to be at diametrically opposed locations relative to the common shaft 66.

Figure 15:
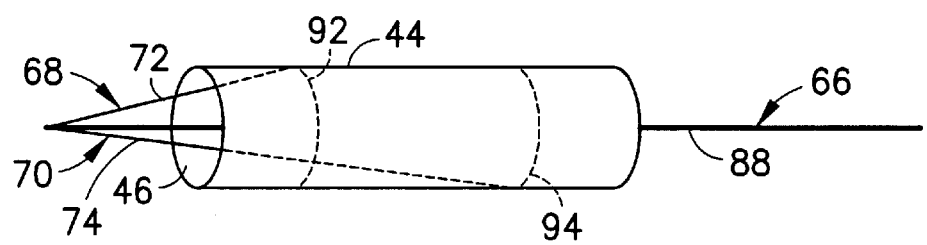
FIG. 15 is a plan view of the second embodiment of the invention with a vascular graft being mounted thereto.

FIG. 15 shows the graft 44 being mounted to the instrument 66. The free ends 80, 86, respectively, of the tines 72, 74 engage the inner surface 46 of the graft 44 at axially-spaced location. The bias applied to the tines 72 and 74 urges the free ends 80, 86 outwardly from the common shaft 66, and as a result, cause the graft 44 to partially expand. As with the first embodiment, it is desired that the graft 44 be sufficiently expanded to allow for entry of an unexpanded stent thereinto. Thus, the free ends 80, 86 must respectively be spaced from the common shaft 88 a distance which is at least as great as half of the outer diameter of the unexpanded stent—i.e. the tines 72, 74 must be formed such that the bias applied to the tines 72, 74 will at least provide for sufficient expansion of the graft 44 to allow for passage of the unexpanded stent into the graft 44.

To prevent movement of the graft 44 relative to the common shaft 66, a length of thread 92, 94 is secured to each of the free ends 80 and 86 which generally defines the shape of a loop. Additionally, the threads 92, 94 are sewn through portions of the graft 44, as shown in FIG. 15. The threads 92, 94 are to be secured to the free ends 80, 86 with both ends of each of the threads 92, 94, respectively engaging the tine 72, 74. The threads 92, 94 are to be secured so that one end thereor will disconnect from the tine 72, 74 upon expansion of the distensible device 58, but not the stent 54.

Although FIG. 15 shows the graft 44 to have a generally cylindrical shape in a semi-expanded state, the graft 44 may not necessarily have such a shape. Referring to FIG. 16, prior to expansion, the graft 44 may have pleats or folds formed therin due to its semi-expanded state. FIG. 16 shows the thread 92 formed to define an elliptical loop secured to the tine 72 and passing in and out of the graft 44 in a sewn configuration. The dashed lines in FIG. 16 represent the graft 44 in a fully expanded state. The graft 44 in a fully expanded state will define an inner radius "r". For use of the invention as described below, the length of the threads 92, 94 must be less than the circumference defined by the fully expanded graft 44. Stated algrebraically, the length of the threads 92, 94, respectively, must be less than 2Πr.

It can be appreciated that although the description of the second embodiment set forth above is directed to the use of two tines 72, 74 and two lengths of thread 92, 94 any number of tines and/or threads may be used. Also, the tines 72, 74 need not be formed to be straight, but only having an end or portion for engaging the graft 44.

It should also be noted that although the tines 72, 74 are shown to extend into the graft 44, the tines 72, 74 may likewise be disposed to be outside of the graft 44. In this variation, the tines 72, 74 actually pull open the graft 44 to the semi-expanded state. This variation must be used cautiously since the tines 72, 74 will contact directly the blood vessel.

The second embodiment of the invention is used in the same arrangement and in the same manner as the first embodiment. Once the loops defined by the threads 92, 94 are ruptured, the common shaft 66 may be advanced so that the tines 72, 74 pull the threads 92, 94, thus ensuring the threads 92, 94 are fully withdrawn from the graft 44. Afterwards, either the catheter 60, which supports the distensible device 58, may be advanced over or the instrument 66 may be retracted into the catheter 60 and the instrument 66 may be removed. The lumen of the catheter 60 must be sufficiently dimensioned to capture the free ends 80 and 86 of the tines 72 and 74, which would be in natural states. The second embodiment may also be used withe the non-self-expanding stent 64.

Figure 17:
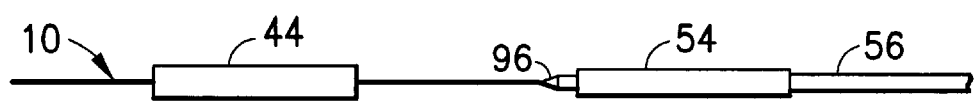
FIG. 17 is a plan view of the third embodiment of the invention arranged with an unexpanded stent.

FIG. 17 is directed to a third embodiment of the invention. The third embodiment encompasses variations of the first two embodiments. With respect to the third embodiment, the structure of the instruments as set forth above remains the same. However, the loops 16 and 18 of the instrument 10 of the first embodiment, and the tines 72 and 74 of the instrument 66 of the second embodiment need not be formed with memory or bias. Instead, the third embodiment merely functions to maintain the graft 44 in a relatively fixed location along the instrument but not provide any impetus to cause the graft 44 to expand. Specifically, with respect to the structure of the first embodiment, the frictional engagement between the structure of the loops 16, 20 and the segments 22, 34 is relied upon. With respect to the structure of the second embodiment, the stitching of the threads 92 and 94 are relied upon to maintain the graft 44 in a relatively fixed position.

Since however the graft 44 will not be forced into a semi-expanded state a catheter must be provided having a sharpened or ramped end 96. FIG. 17 depicts an exemplary illustration of the third embodiment of the invention. The graft 44 is shown to be supported by the instrument 10 and the stent 54 is shown to be supported by the catheter 56. The catheter 56 is provided with the sharpened tip 96. In use, as described above with respect to the first and second embodiments, upon introducing the stent 54 into the graft 44, the tip 96 would be forced into the graft 44 and cause expansion thereof. Further advancement of the tip 96 will cause the tip 96 to slip under the loops 16, 18 (not shown) with the catheter 56 and the stent 54 following. If variations of the embodiments are used and the non-self expanding stent 64 is utilized, the catheter bearing the stent 64 is formed with the tip 96.

As is readily apparent, numerous modifications and changes may readily occur to those skilled in the art, and hence it is not desired to limit the invention to the exact construction operation as shown and described, in accordingly all suitable modification equivalents may be resorted to falling within the scope of the invention as claimed.

What is claimed is:

1. A device for treating blood vessel anomalies, said device comprising a tubular vascular graft, the vascular graft being formed about a longitudinal axis with an inner surface extending the length of the vascular graft about the longitudinal axis, and a first flexible guidewire formed to define a collapsible loop and a segment, said loop being resiliently formed with memory to self-expand from a collapsed state to a natural, non-collapsed state, said loop encircling the longitudinal axis of the vascular graft and supporting portions of the inner surface of the vascular graft, wherein a first portion of said segment is integrally connected to said loop and extends therefrom in a direction continuously angular to the longitudinal axis of the graft, a second portion of said segment is integrally connected to and extends from said first portion through at least a portion of the vascular graft.

2. A device as in claim 1, said loop being formed to bias said supported portions of the vascular graft into a spaced relationship such that an open passage extends through at least a portion of the vascular graft.

3. A device as in claim 1, wherein the vascular graft is formed with opposing ends spaced along the longitudinal axis, wherein said first portion of said segment extends from said loop in a direction generally towards one end of the vascular graft and said second portion of said segment extends from said first portion in a direction generally towards the opposing end of the vascular graft.

4. A device as in claim 1 further comprising a second flexible guidewire, said second guidewire formed to define a collapsible loop and a segment, said loop of said second guidewire encircling the longitudinal axis of the vascular graft and supportingly engaging portions of the inner surface of the vascular graft, wherein, a first portion of said segment of said second guidewire is integrally connected to said loop of said second guidewire and extends therefrom in a direction continuously angular to the longitudinal axis of the graft, a second portion of said segment of said second guidewire is integrally connected to and extends from said first portion of said second guidewire through at least a portion of the vascular graft.

5. A device as in claim 4, wherein, said loops being resiliently formed with memory to collectively bias said engaged portions of the inner surface of the vascular graft into a spaced relationship such that an open passage extends through at least a portion of the vascular graft.

6. A device as in claim 4, wherein said second portion of said first guidewire extends through said loop of said second guidewire.

7. A device as in claim 6, wherein said second portion of said first guidewire extends through said loop of said first guidewire.

8. A device as in claim 7, wherein said second portion of said second guidewire extends through said loop of said second guidewire.

9. A device as in claim 8, wherein said second portion of said second guidewire extends through said loop of said first guidewire.

10. A device as in claim 4, wherein said loops are spaced apart along the longitudinal axis of the vascular graft.

11. A device as in claim 1, wherein said loop is defined by a predetermined length of said guidewire extending from a first end thereof, said first end being frangibly connected to the connection of said loop and said first portion of said guidewire.

12. A device for treating blood vessel anomalies, said device comprising a tubular vascular graft formed with an inner surface, and a first flexible guidewire formed to define a tine and a segment, said tine having first and second ends, wherein said first end of said tine being hingedly connected to said segment with said tine being selectively pivotable relative to said segment, the hinged connection generating a bias which urges said second end of said tine radially away from said segment to support a portion of the inner surface of the vascular graft.

13. A device as in claim 12 further comprising a second flexible guidewire, said second guidewire formed to define a tine and a segment, said tine of said second guidewire having first and second ends, said first end of said tine of said second guidewire being hingedly connected to said segment of said second guidewire, said second end of said tine of second guidewire being spaced from said segment of said second guidewire and supportingly engaging a portion of the inner surface of the graft.

14. A device as in claim 13, wherein said segments are joined to define a single unitary shaft.

15. A device as in claim 14, wherein said second ends of said tines are spaced from said shaft in diammetrically opposed directions, said directions being both normal to said shaft.

16. A device as in claim 13, wherein said tine of said first guidewire defines a first length, said tine of said second guidewire defines a second length, said first length being greater than said second length.

* * * * *